US005705483A

United States Patent [19]
Galloway et al.

[11] Patent Number: 5,705,483
[45] Date of Patent: Jan. 6, 1998

[54] GLUCAGON-LIKE INSULINOTROPIC PEPTIDES, COMPOSITIONS AND METHODS

[75] Inventors: John A. Galloway, Indianapolis; James A. Hoffmann, Greenwood, both of Ind.

[73] Assignee: Eli Lilly and Company, Indianapolis, Ind.

[21] Appl. No.: 407,831

[22] Filed: Mar. 21, 1995

Related U.S. Application Data

[63] Continuation-in-part of Ser. No. 164,277, Dec. 9, 1993, abandoned.

[51] Int. Cl.$^6$ .................. A61K 38/26; C07K 14/605
[52] U.S. Cl. ..................... 514/12; 530/308; 530/324
[58] Field of Search ............................. 530/308, 324; 514/12

[56] References Cited

U.S. PATENT DOCUMENTS

| | | |
|---|---|---|
| 4,347,374 | 8/1982 | Kollonitsch et al. . |
| 5,118,666 | 6/1992 | Habener . |
| 5,120,712 | 6/1992 | Habener . |

FOREIGN PATENT DOCUMENTS

| | | |
|---|---|---|
| 0619322A3 | 3/1996 | European Pat. Off. . |
| WO91/11457 | 8/1991 | WIPO . |
| WO92/18531 | 10/1992 | WIPO . |
| WO93/18786 | 9/1993 | WIPO . |
| WO93/25579 | 12/1993 | WIPO . |
| WO95/05848 | 8/1994 | WIPO . |
| WO95/05848 | 3/1995 | WIPO . |

OTHER PUBLICATIONS

Komatsu, R., et al., *Diabetes*, 38:902–905 (1989).
Orskov, C., et al., *J. Biol. Chem.*, 264(22):12826–12829 (1989).
Majsov, S., *Int. J. Peptide Protein Res.*, 40–333–343 (1989).
Holz, G.G., et al., *Nature*, 361:362–365 (1993).
Orskov, C., *Diabetologia*, 35:701–711 (1992).
Mentlein, R., et al., *Eur. J. Biochem.*, 214:829–835 (1993).
Handbook of Experimental Pharmacology, Springer-Verlag, Hasselblatt, et al., (Eds.), 32(2):729–777 (1975).
Nauck, M.A., et al., *J. Clin. Invest.*, 91:301–307 (1993).
Nauck, M.A., et al., *Diabetologia*, 36:741–744 (1993).
Gutniak, M., et al., *N. E. J. Med.*, 326(20):1316–1322, (1992).
Thorens, B., et al., *Diabetes*, 42:1219–1225 (1993).
Levine–Pinto, H., et al., *Biochem. Biophys. Res. Commun.*, 103(4) :1121–1130 (1981).
Owa, T., et al., *Chem. Letters*: 873–874 (1988).
Altman, J., et al., *Synthetic Commun.*, 19(11 & 12) :2069–2076 (1989).
O'Donnell, M.J., et al., *Synthetic Commun.*, 19 (7 & 8) :1157–1165 (1989).
Galloway, J.A., *Diabetes Care*, 13:1209–1239, (1990).
Galloway, J.A., et al., *Clin. Therap.*, 12:460–472 (1990).
Suzuki, S., et al., *Endocrinology*, 125, 3109–3114, (1990).
Ananthanancayanan, V.V., et al., *Mol. Biol. Cell* (Supp) 3, 250A (1992).
Epand, R.M., *Mol. Pharmacol.* 22, 105–108 (1982).
Pridal, L. et al., "Absorption of glucagon–like peptide–1 can be protracted by zinc or protamine", International Journal of Pharmaceutics 136 (1996) 53–59.

*Primary Examiner*—Paula K. Hutzell
*Assistant Examiner*—Benet Prickril
*Attorney, Agent, or Firm*—Ronald S. Maciak; David E. Boone

[57] ABSTRACT

The present invention provides novel complexes consisting of certain GLP-1 molecules associated with a divalent metal cation that is capable of co-precipitating with a GLP-1 molecule. Pharmaceutical compositions and methods of using such complexes for enhancing the expression of insulin in B-type islet cells is claimed, as is a method for treating maturity onset diabetes mellitus in mammals, particularly humans.

4 Claims, No Drawings

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 29..30
        ( D ) OTHER INFORMATION: /label=modified-site
            / note="The arginine residue at position 30 is
            modified so as to replace the terminal carboxyl
            group with an amine."

( x i ) SEQUENCE DESCRIPTION: SEQ ID NO:1:

```
His Ala Glu Gly Thr Arg Thr Ser Asp Val Ser Ser Tyr Leu Glu Gly
 1               5                  10                  15

Gln Ala Ala Lys Glu Phe Ile Ala Trp Leu Val Lys Gly Arg
             20                  25                  30
```

GLUCAGON-LIKE INSULINOTROPIC PEPTIDES, COMPOSITIONS AND METHODS

This application is a continuation-in-part of Galloway et al., U.S. Ser. No. 08/164,277, filed Dec. 9, 1993, now abandoned.

BACKGROUND OF THE INVENTION

This invention relates to the field of pharmaceutical and organic chemistry and provides novel compounds, and pharmaceutical compositions thereof, which are useful for enhancing the expression of insulin from mammalian pancreatic B-type islet cells and for treating maturity onset diabetes mellitus in a meal.

The endocrine secretions of the pancreatic islets are under complex control not only by blood-borne metabolites (glucose, amino acids, catecholamines, etc.), but also by local paracrine influences. The major pancreatic islet hormones (glucagon, insulin and somatostatin) interact amongst their specific cell types (A, B, and D cells, respectively) to modulate secretory responses mediated by the aforementioned metabolites. Although insulin secretion is predominantly controlled by blood levels of glucose, somatostatin inhibits glucose-mediated insulin secretory responses. In addition to the proposed interislet paracrine regulation of insulin secretion, there is evidence to support the existence of insulinotropic factors in the intestine. This concept originates from the observations that glucose taken orally is a much more potent stimulant of insulin secretion than is a comparable amount of glucose given intravenously.

The human hormone glucagon is a 29-amino acid peptide hormone produced in the A-cells of the pancreas. The hormone belongs to a multi-gene family of structurally related peptides that include secretin, gastric inhibitory peptide, vasoactive intestinal peptide and glicentin. These peptides variously regulate carbohydrate metabolism, gastrointestinal mobility and secretory processing. The principal recognized actions of pancreatic glucagon, however, are to promote hepatic glycogenolysis and glyconeogenesis, resulting in an elevation of blood sugar levels. In this regard, the actions of glucagon are counter regulatory to those of insulin and may contribute to the hyperglycemia that accompanies Diabetes mellitus [(Lund, P. K., et el., *Proc. Natl. Aced. Sci. U.S.A.,* 79:345–349 (1982)].

Glucagon has been found to be capable of binding to specific receptors which lie on the surface of insulin producing cells. Glucagon, when bound to these receptors, stimulates the rapid synthesis of cAMP by these cells. cAMP, in turn, has been found to stimulate insulin expression [Korman, L. Y., et al., *Diabetes,* 34:717-722 (1985)]. Insulin acts to inhibit glucagon synthesis [Ganong, W. F., *Review of Medical Physiology,* Lange Publications, Los Altos, Calif., p. 273 (1979)]. Thus, the expression of glucagon is carefully regulated by insulin, and ultimately by the serum glucose level.

The glucagon gene is initially translated from a 360 base pair precursor to form the polypeptide, preproglucagon [Lund, et al., *Proc. Natl. Aced. Sci. U.S.A.* 79:345–349 (1982)]. This polypeptide is subsequently processed to form proglucagon. Patzelt, C., et el., *Nature,* 282:260-266 (1979), demonstrated that proglucagon was subsequently cleaved into glucagon and a second polypeptide. Subsequent work by Lund, P. K., et el., Lopez L. C., et al., *Proc. Natl. Acad. Sci. U.S.A.,* 80:5485–5489 (1983), and Bell, G. I., et el., *Nature* 302:716–718 (1983), demonstrated that the proglucagon molecule was cleaved immediately after lysine-arginine dipeptide residues. Studies of proglucagon produced by channel catfish (*Ictalurus punctata*) indicated that glucagon from this animal was also proteolytically cleaved after adjacent lysine-arginine dipeptide residues [Andrews P. C., et al., *J. Biol. Chem.,* 260:3910–3914 (1985), Lopez, L. C., et al., *Proc. Natl. Acad. Sci. U.S.A.,* 80:5485–5489 (1983)]. Bell, G. I., et al., supra, discovered that mammalian proglucagon was cleaved at lysine-arginine or arginine-arginine dipeptides, and demonstrated that the proglucagon molecule contained three discrete and highly homologous peptide molecules which were designated glucagon, glucagon-like peptide 1 (GLP-1) and glucagon-like peptide 2 (GLP-2). Lopez, et al., concluded that glucagon-like peptide 1 was 37 amino acid residues long and that glucagon-like peptide 2 was 34 amino acid residues long. Analogous studies on the structure of rat preproglucagon revealed a similar pattern of proteolytic cleavage between adjacent lysine-arginine or arginine—arginine dipeptide residues, resulting in the formation of glucagon, GLP-1 and GLP-2 [Heinrich, G., et al., *Endocrinol.,* 115:2176–2181 (1984)]. Human, rat, bovine, and hamster sequences of GLP-1 have been found to be identical [Ghiglione, M., et al., *Diabetologia,* 27:599–600 (1984)].

The conclusion reached by Lopez, et al., regarding the size of GLP-1 was confirmed by the work of Uttenthal, L. O., et al., *J. Clin. Endocrinol. Metabol.,* 61:472–479 (1985). Uttenthal, et al., examined the molecular forms of GLP-1 which were present in the human pancreas. Their research shows that GLP-1 and GLP-2 are present in the pancreas as 37 amino acid and 34 amino acid peptides, respectively.

The similarity between GLP-1 and glucagon suggested to early investigators that GLP-1 might have biological activity. Although some investigators found that GLP-1 could induce rat brain cells to synthesize cAMP [Hoosein, N. M., et al., *Febs Lett.* 178:83–86 (1984)], other investigators failed to identify any physiological role for GLP-1 (Lopez, L. C., et al.). The failure to identify any physiological role for GLP-1 caused some investigators to question whether GLP-1 was in fact a hormone and whether the relatedness between glucagon and GLP-1 might be artifactual.

Variants of GLP-1 (7–37) and analogs thereof, also have been disclosed. These variants and analogs include, for example, $Gln^9$-GLP-1 (7-37), D-$Gln^9$-GLP-1 (7-37), acetyl-$Lys^9$-GLP-1 (7-37), $Thr^{16}$-$Lys^{18}$-GLP-1 (7-37), $Lys^{18}$-GLP-1 (7-37) and the like, and derivatives thereof including, for example, acid addition salts, carboxylate salts, lower alkyl esters, and amides [see, e.g., WO 91/11457]. Generally, the various disclosed forms of GLP-1 are known to stimulate insulin secretion (insulinotropic action) and cAMP formation [see, e g., Mojsov, S., *Int. J. Peptide Protein Research,* 40:333–343 (1992)].

More importantly, multiple authors have demonstrated the nexus between laboratory experimentation and mammalian, particularly human, insulinotropic responses to exogenous administration of GLP-1, particularly GLP-1 (7–36)NH$_2$ and GLP-1 (7-37) [see, e.g., Nauck, M. A., et al., *Diabetologia,* 36:741–744 (1993); Gutniak, M., et al., *New England J. of Medicine,* 326(20):1316–1322 (1992); Nauck, M. A., et al., *J. Clin. Invest.,* 91:301–307 (1993); and Thorens, B., et al., *Diabetes,* 42:1219–1225 (1993)].

More particularly, the fundamental defects identified as causing hyperglycemia in maturity onset diabetes are impaired secretion of endogenous insulin and resistance to the effects of insulin by muscle and liver [Galloway, J. S., *Diabetes Care,* 13:1209–1239, (1990)]. The latter defect results in excessive production of glucose from the liver.

Thus, whereas a normal individual releases glucose at the rate of approximately 2 mg/kg/minute, in patients with maturity onset diabetes, this amount usually exceeds 2.5 mg/kg/minute resulting in a net excess of at least 70 grams of glucose per 24 hours. The fact that there exists exceedingly high correlations between hepatic glucose production, the fasting blood glucose and overall metabolic control as indicated by glycohemoglobin measurements [Galloway, J. A., supra; and Galloway, J. A., et al., *Clin. Therap.*, 12:460= 472 (1990)], it is readily apparent that control of the fasting blood glucose is a sine quo non for achieving overall normalization of metabolism sufficient to prevent the complication of hyperglycemia. In view of the fact that present forms of insulin rarely normalize hepatic glucose production without producing significant hyperinsulinemia and hypoglycemia (Galloway, J. A., and Galloway, J. A., et al., Supra) alternative approaches are needed.

Intravenous infusions of GLIP-1 (7-36)NH$_2$ to produce twice normal serum concentrations have been demonstrated to produce the effects indicated in the table below:

|  | Normal Subjects | Patients With Maturity Onset Diabetes |
|---|---|---|
| Meal glycemia(1) | Unchanged | Reduced |
| Fasting glycemia(2) | — | Reduced |
| Fasting glucagon(2) | — | Reduced |
| Post-prandial glucagon(1) | — | Reduced |
| Endogenous insulin secretion in response to a meal(1) | Unchanged | Increased |
| Free fatty acids | Reduced(3) | Reduced(2) |

(1)Gutniak, M., et al., supra.
(2)Nauck, M.A., et al., Diabetologia, supra.
(3)Orskov, C., et al., Diabetes, 42:658–661, (1993).

However, the long-term stability of GLP-1, particularly GLP-1 as a component of a pharmaceutical composition for administration to mammals, is questionable. In fact, when stored at the low temperature of 4° C., by-products of GLP-1 (7-37) have been found as early as eleven months after sample preparation (Mojsov, S., supra). Thus, there exists a need for a more stable GLP-1 compound which can safely be administered to mammals in need of such treatment.

Furthermore, the biological half-life of GLP-1 molecules, particularly those molecules which are affected by the activity of dipeptidyl-peptidase IV (DPP IV) is quite short. For example, the biological half-life of GLP-1 (7-37) is a mere 3 to 5 minutes (U.S. Pat. No. 5,118,666), and is further influenced by its rapid absorption following parenteral administration to a mammal. Thus, there also exists a need for a GLP-1 compound which delays absorption following such administration.

Accordingly, the present invention provides compounds which satisfy the aforementioned stability requirements. The compounds of the present invention also provide delayed absorption following parenteral administration and, consequently, should have extended biological half-lives. Also provided are pharmaceutical compositions of the compounds of the present invention, as well as methods for using such compounds.

SUMMARY OF THE INVENTION

The present invention provides a complex consisting of a divalent metal cation associated with and capable of co-precipitating with a compound of the formula:

R$_1$-X-Glu-Gly-Thr-Phe-Thr-Ser-Asp-Val-Ser-Ser-
Tyr-Leu-Y-Gly-Gln-Ala-Ala-Lys-Z-Phe-Ile-Ala-Trp-
Leu-Val-Lys-Gly-Arg-R$_2$ (SEQ ID NO: 1)

wherein:

R$_1$ is selected from the group consisting of L-histidine, D-histidine, desamino-histidine, 2-amino-histidine, β-hydroxy-histidine, homohistidine, alpha-fluoromethyl-histidine, and alpha-methyl-histidine;

X is selected from the group consisting of Ala, Gly, Val, Thr, Ile, and alpha-methyl-Ala;

Y is selected from the group consisting of Glu, Gln, Ala, Thr, Ser, and Gly;

Z is selected from the group consisting of Glu, Gln, Ala, Thr, Ser, and Gly;

R$_2$ is selected from the group consisting of NH$_2$, and Gly-OH; providing that the compound has an isoelectric point in the range from about 6.0 to about 9.0 and further providing that when R$_1$ is His, X is Ala, Y is Glu, and Z is Glu, R$_2$ must be NH$_2$.

Also provided by the present invention is a pharmaceutical composition comprising a compound of the present invention in combination with one or more pharmaceutically acceptable carriers, diluents, or excipients.

The present invention further provides a method for enhancing the expression of insulin comprising providing to a mammalian pancreatic B-type islet cell an effective amount of a compound of the present invention, as well as a method of treating maturity onset diabetes mellitus which comprises administering to a mammal in need of such treatment an effective amount of a compound of the present invention.

DETAILED DESCRIPTION OF THE INVENTION

One aspect of the present invention provides a complex consisting of a GLP-1 molecule having an isoelectric point in the range from about 6.0 to about 9.0, complexed with a divalent metal cation.

As used in the present specification, the term "GLP-1 molecule" refers to naturally-occurring GLP-1 (7-36)NH$_2$, GLP-1 (7-37), natural and unnatural functional analogs and derivatives thereof, and salts thereof. The amino acid sequence of GLP-1 (7-36)NH$_2$ is well known in the art, but is presented below as a convenience to the reader:

His$^7$-Ala-Glu-Gly$^{10}$-Thr-Phe-Thr-Ser-Asp$^{15}$-Val-
Ser-Ser-Tyr-Leu$^{20}$-Glu-Gly-Gln-Ala-Ala$^{25}$-Lys-Glu-
Phe-Ile-Ala$^{30}$-Trp-Leu-Val-Lys-Gly$^{35}$-Arg-NH$_2$
(SEQ ID NO: 1).

For GLP-1 (7-37), the carboxy-terminal amide functionality of Arg$^{36}$ is displaced with Gly at the 37th position of the GLP-1 (7-36)NH$_2$ molecule.

In addition, the existence and preparation of a multitude of protected, unprotected, and partially protected natural and unnatural functional analogs and derivatives of GLP-1 (7-36)NH$_2$ and GLP-1 (7-37) molecules have been described in the art [see, e.g., U.S. Pat. No. 5,120,712 and 5,118,666, which are herein incorporated by reference, and Orskov, C., et al., *J. Biol. Chem.*, 264(22):12826–12829 (1989) and WO 91/11457 (Buckley, D. I., et al., published August 8, 1991)].

As known in the art, amino acid residues may be in their protected form in which both amino and carboxy groups possess appropriate protecting groups, partially-protected form in which either amino or carboxy groups possess appropriate protecting groups, or unprotected form in which neither amino nor carboxy groups possess an appropriate protecting group. Numerous reactions for the formation and removal of such protecting groups are described in a number of standard works including, for example, "Protective Groups in Organic Chemistry", Plenum Press (London and New York, 1973); Green, T. H., "Protective Groups in Organic Synthesis", Wiley (New York, 1981); and "The Peptides", Vol. I, Schröder and Lübke, Academic Press (London and New York, 1965).

Representative amino protecting groups include, for example, formyl, acetyl, isopropyl, butoxycarbonyl, fluorenylmethoxycarbonyl, carbobenzyloxy, and the like.

Representative carboxy protecting groups include, for example, benzyl ester, methyl ester, ethyl ester, t-butyl ester, p-nitro phenyl ester, and the like.

In addition to protected forms in which both amino and carboxy groups possess appropriate protecting groups, the term "protected" also refers to those GLP-1 molecules in which the activity of dipeptidyl-peptidase IV is resisted or inhibited [see, e.g., Mentlein, R., et al., Eur. J. Biochem., 214:829–835 (1993)]. In addition to GLP-1(7-36)NH$_2$, molecules which are protected from the activity of DPP IV are preferred, and Gly$^8$-GLP-1(7-36)NH$_2$, Val$^8$-GLP-1(7-37)OH, α-methyl-Ala$^8$-GLP-1(7-36)NH$_2$, and Gly$^8$-Gln$^{21}$-GLP-1(7-37)OH are more preferred.

Derivatives of naturally-occurring GLP-1 molecules are those peptides which are obtained by fragmenting a naturally-occurring sequence, or are synthesized based upon a knowledge of the sequence of the naturally-occurring amino acid sequence of the genetic material (DNA or RNA) which encodes this sequence. The term "derivatives" also includes chemical modification of natural or unnatural GLP-1 molecules. Processes for preparing these derivatives are well known to organic and peptide chemists of ordinary skill (see, e.g., WO 91/11457, supra).

GLP-1 molecules of the present invention also include analogs of GLP-1 (7-36)NH$_2$ and GLP-1 (7-37) in which one or more amino acids which are not present in the original sequence are added or deleted, and derivatives thereof. Specifically, His and desamino-histidine are preferred for R$_1$, so long as the overall isoelectric point of the molecule is in the range of about 6 to 9. Ala, Gly, and Val are preferred at the "X" position, so long as the overall isoelectric point of the molecule is in the range of about 6 to 9. Likewise, Glu, and Gln are preferred at the "Y" position, so long as the overall isoelectric point of the molecule is in the range of about 6 to 9. Also, Glu, and Gln are preferred at the "Z" position, so long as the overall isoelectric point of the molecule is in the range of about 6 to 9. Finally, Gly-OH is preferred for R$_2$, so long as the overall isoelectric point of the molecule is in the range of about 6 to 9.

Furthermore, the present invention includes a salt form of a GLP-1 molecule. A GLP-1 of this invention can possess a sufficiently acidic, a sufficiently basic, or both functional groups, and accordingly react with any of a number of inorganic bases, and inorganic and organic acids, to form a salt. Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like. Preferred acid addition salts are those formed with mineral acids such as hydrochloric acid and hydrobromic acid, and, especially, hydrochloric acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, and the like. The salt forms are particularly preferred.

Of course, when the compounds of this invention are used for pharmacotherapeutic purposes, those compounds may also be in the form of a salt, but the salt must be pharmaceutically acceptable.

Thus, GLP-1 molecules of the present invention include inter alia, those GLP-1 molecules which functionally demonstrate insulinotropic activity. The term "insulinotropic activity" relates to the ability of a substance to stimulate, or cause the stimulation of, the synthesis or expression of the hormone insulin.

The insulinotropic property of a compound may be determined by providing that compound to animal cells, or injecting that compound into animals and monitoring the release of immunoreactive insulin (IRI) into the media or circulatory system of the animal, respectively. The presence of IRI is detected through the use of a radioimmunoassay which can specifically detect insulin.

Although any radioimmunoassay capable of detecting the presence of IRI may be employed, it is preferable to use a modification of the assay method of Albano, J. D. M., et al., Acta Endocrinoi., 70:487-509 (1972). In this modification, a phosphate/albumin buffer with a pH of 7.4 is employed. The incubation is prepared with the consecutive addition of 500 μl of phosphate buffer, 50 μl of perfusate sample or rat insulin standard in perfusate, 100 μl of anti-insulin antiserum (Wellcome Laboratories; 1:40,000 dilution), and 100 μl of [$^{125}$I] insulin, giving a total volume of 750 μl in a 10×75 mm disposable glass tube. After incubation for 2–3 days at 4° C., free insulin is separated from antibody-bound insulin by charcoal separation. The assay sensitivity is 1–2 uU/mL. In order to measure the release of IRI into the cell culture medium of cells Grown in tissue culture, one preferably incorporates radioactive label into proinsulin. Although any radioactive label capable of labelling a polypeptide can be used, it is preferable to use $^3$H leucine in order to obtain labelled proinsulin. Labelling can be done for any period of time sufficient to permit the formation of a detectably labelled pool of proinsulin molecules; however, it is preferable to incubate cells in the presence of radioactive label for a 60 minute time period.

Although many cell lines capable of expressing insulin can be used for determining whether a compound has an insulinotropic effect, it is preferable to use rat insulinoma cells, and especially RIN-38 rat insulinoma cells. Such cells can be grown in any suitable medium; however, it is preferable to use DME medium containing 0.1% BSA and 25 mM glucose.

The insulinotropic property of a compound may also be determined by pancreatic infusion. The in situ isolated perfused rat pancreas preparation is a modification of the method of Penhos, J. C., et al., Diabetes, 18:733–738 (1969). Fasted male Charles River strain albino rats, weighing 350–600 g, are anesthetized with an intraperitoneal injection of Amytal Sodium (Eli Lilly and Co.: 160 ng/kg). Renal, adrenal, gastric, and lower colonic blood vessels are ligated. The entire intestine is resected except for about four cm of duodenum and the descending colon and rectum. Therefore, only a small part of the intestine is perfused, minimizing possible interference by enteric substances with glucagon-like immunoreactivity. The perfusate is a modified Krebs-Ringer bicarbonate buffer with 4% dextran T70 and 0.2% bovine serum albumin (fraction V), and is bubbled with 95% $O_2$ and 5% $CO_2$. A nonpulsatile flow, 4-channel roller bearing pump (Buchler polystatic, Buchler Instruments Division, Nuclear-Chicago Corp.) is used, and a switch from one perfusate source to another is accomplished by switching a 3-way stopcock. The manner in which perfusion is performed, monitored, and analyzed follow the method of Weir, G. C., et al., J. Clin. Inestigat. 54:1403–1412 (1974), which is hereby incorporated by reference.

The GLP-1 molecules of the present invention are required to possess a histidine functionality at the amino terminus. GLP-1 molecules of the present invention may also possess a modified histidine functionality in lieu of the required histidine functionality.

The term "modified histidine" refers to a histidine functionality which has been chemically or biologically altered or an altered histidine functionality which has been synthesized de novo, but which retains its metal binding properties.

Numerous such modified histidine functionalities and their preparation are known in the art and include, for example, D-histidine (WO 91/11457), desamino-histidine (WO 92/18531), 2-amino-histidine [Levine-Pinto, H., et al., Biochem. Biophys. Res. Commun., 103(4):1121–1130 (1981)], β-hydroxy-L-histidine [Owa, T, et al., Chemistry Letters, pp. 1873–1874 (1988)], L-homohistidine [Altman, J., et al., Synthetic Commun., 19(11&12):2069–2076 (1989) ], α-fluoromethyl-histidine (U.S. Pat. NO. 4,347,374), and α-methylhistidine [O'Donnell, M. J., Synthetic Commun., 19(7&8):1157–1165 (1989)].

The GLP-1 molecules of the present invention further are required to have an isoelectric point in the range from about 6.0 to about 9.0. Numerous GLP-1 molecules having an isoelectric point in this range have been disclosed and include, for example:

GLP-1 (7-36)$NH_2$ $Gly^8$-GLP-1 (7-36)$NH_2$ $Gln^9$-GLP-1 (7-37)

D-$Gln^9$-GLP-1 (7-37)

acetyl-$Lys^9$-GLP-1 (7-37)

$Thr^9$-GLP-1 (7-37)

D-$Thr^9$-GLP-1 (7-37)

$Asn^9$-GLP-1 (7-37)

D-$Asn^9$-GLP-1 (7-37)

$Ser^{22}$-$Art^{23}$-Arg24-$Gln^{26-GLP-1}$ (7-37)

$Thr^{16}$-$Lys^{18}$-GLP-1 (7-37)

$Lys^{18}$-GLP-1 (7-37)

$Arg^{23}$-GLP-1 (7-37)

$Arg^{24}$-GLP-1 (7-37), and the like (see, e.g., WO 91/11457, supra). In addition, GLP-1 molecules of the present invention, when possessing each of the above-referenced modified histidine functionalities in lieu of the histidine functionality, have isoelectric points which fall within the above-defined range. Methods for calculating or experimentally determining the isoelectric point of other GLP-1 molecules are known to one of ordinary skill in the art.

Methods for preparing the GLP-1 molecules of the present invention also are well known to an ordinarily skilled peptide chemist.

In one method, GLP-1 molecules are prepared by the well-known solid phase peptide synthetic schemes described by Merrifield, J. M., Chem. Soc., 85:2149 (1962), and Stewart and Young, Solid Phase Peptide Synthesis, pp. 24–66, Freeman (San Francisco, 1969). However, it also is possible to obtain fragments of the proglucagon polypeptide or of GLP-1 (1–37) by fragmenting the naturally-occurring amino acid sequence using, for example, a proteolytic enzyme. Further, it is possible to obtain the desired fragments of the proglucagon peptide or of GLP-1 (1–37) through the use of recombinant DNA technology as disclosed by Maniatis, T., et al., Molecular Biology: A Laboratory Manual, CSH (Cold Spring Harbor, 1982).

Likewise, the state of the art in molecular biology provides the ordinarily skilled artisan another means by which compounds of the present invention can be obtained. Although it may be produced by solid phase peptide synthesis or recombinant methods, recombinant methods may be preferable because higher yields are possible. The basic steps in recombinant production are:

a) isolating a natural DNA sequence encoding a GLP-1 molecule or constructing a synthetic or semi-synthetic DNA coding sequence for a GLP-1 molecule, b) placing the coding sequence into an expression vector in a manner suitable for expressing proteins either alone or as a fusion proteins, c) transforming an appropriate eukaryotic or prokaryotic host cell with the expression vector, d) culturing the transformed host cell under conditions that will permit expression of a GLP-1 molecule, and e) recovering and purifying the recombinantly produced GLP-1 molecule.

As previously stated, the coding sequences may be wholly synthetic or the result of modifications to the larger, native glucagon-encoding DNA. A DNA sequence that encodes preproglucagon is presented in Lund, et al., Proc. Nat. Acad. Sci. U.S.A. 79:345–349 (1982) and may be used as starting material in the semisynthetic production of the compounds of the present invention by altering the native sequence to achieve the desired results.

Synthetic genes, the in vitro or in vivo transcription and translation of which results in the production of a GLP-1 molecule, may be constructed by techniques well known in the art. Owing to the natural degeneracy of the genetic code, the skilled artisan will recognize that a sizable yet definite number of DNA sequences may be constructed, all of which encode GLP-1 molecules.

The methodology of synthetic gene construction is well known in the art. See Brown, et al. (1979) Methods in Enzymology, Academic Press, N.Y., Vol. 68, pgs. 109–151. DNA sequences that encode a GLP-1 molecule can be designed based on the amino acid sequences herein disclosed. Once designed, the sequence itself may be generated using conventional DNA synthesizing apparatus such as the Model 380A or 380B DNA synthesizers (PE-Applied Biosystems, Inc., 850 Lincoln Center Drive, Foster City, Calif. 94404).

To effect expression of a GLP-1 molecule, one inserts the engineered synthetic DNA sequence in any one of many appropriate recombinant DNA expression vectors through the use of appropriate restriction endonucleases. See generally Maniatis et al. (1989) Molecular Cloning; A Laboratory Manual, Cold Springs Harbor Laboratory Press, N.Y., Vol.

1–3. Restriction endonuclease cleavage sites are engineered into either end of the GLP-1 molecule-encoding DNA to facilitate isolation from, and integration into, known amplification and expression vectors. The particular endonucleases employed will be dictated by the restriction endonuclease cleavage pattern of the parent expression vector to be employed. The choice of restriction sites are chosen so as to properly orient the coding sequence with control sequences to achieve proper in-frame reading and expression of the protein of interest. The coding sequence must be positioned so as to be in proper reading frame with the promoter and ribosome binding site of the expression vector, both of which are functional in the host cell in which the protein is to be expressed.

To achieve efficient transcription of the synthetic gene, it must be operably associated with a promoter-operator region. Therefore, the promoter-operator region of the synthetic gene is placed in the same sequential orientation with respect to the ATG start codon of the synthetic gene.

A variety of expression vectors useful for transforming prokaryotic and eukaryotic cells are well known in the art. See *The Promega Biological Research Products Catalogue* (1992) (Promega Corp., 2800 Woods Hollow Road, Madison, Wis., 53711–5399); and *The Stratagene Cloning Systems Catalogue* (1992) (Stratagene Corp., 11011 North Torrey Pines Road, La Jolla, Calif., 92037). Also, U.S. Pat. No. 4,710,473 describes circular DNA plasmid transformation vectors useful for expression of exogenous genes in *E. coli* at high levels. These plasmids are useful as transformation vectors in recombinant DNA procedures and (a) confer on the plasmid the capacity for autonomous replication in a host cell;

(b) control autonomous plasmid replication in relation to the temperature at which host cell cultures are maintained;

(c) stabilize maintenance of the plasmid in host cell populations;

(d) direct synthesis of a protein prod. indicative of plasmid maintenance in a host cell population;

(e) provide in series restriction endonuclease recognition sites unique to the plasmid; and (f) terminate mRNA transcription.

These circular DNA plasmids are useful as vectors in recombinant DNA procedures for securing high levels of expression of exogenous genes.

Having constructed an expression vector for a GLP-1 molecule, the next step is to place the vector into a suitable cell and thereby construct a recombinant host cell useful for expressing the polypeptide. Techniques for transforming cells with recombinant DNA vectors are well known in the art and may be found in such general references as Maniatis, et al. supra. Host cells made be constructed from either eukaryotic or prokaryotic cells.

Prokaryotic host cells generally produce the protein at higher rates and are easier to culture. Proteins which are expressed in high-level bacterial expression systems characteristically aggregate in granules or inclusion bodies which contain high levels of the overexpressed protein. Such protein aggregates typically must be solubilized, denatured and refolded using techniques well known in the art. See Kreuger, et al. (1990) in *Protein Folding*, Gierasch and King, eds., pgs 136–142, American Association for the Advancement of Science Publication No. 89–18S, Washington, D.C.; and U.S. Pat. No. 4,923,967.

Once the desired GLP-1 molecule is prepared, providing it has an isoelectric point in the range from about 6.0 to about 9.0, complexes of the present invention are prepared by complexing a desired GLP-1 molecule with a divalent metal cation via well known methods in the art. Such metal cations include, for example, $Zn^{++}$, $Mn^{++}$, $Fe^{++}$, $Co^{++}$, $Cd^{++}$, $Ni^{++}$, and the like. Of the metal cations, $Zn^{++}$ is preferred.

Generally, a desired GLP-1 molecule, having the required isoelectric point, is combined with a mixture of an appropriate buffer and an appropriate form of a metal cation.

Appropriate buffers are those which will maintain the mixture at a pH range from about 6.0 to about 9.0, but which will not interfere with the reaction. Preferred buffers include Goode's buffers, particularly HEPES, and Tris and Tris acetate.

Appropriate forms of metal cations are any form of a divalent metal cation which is available to form a complex with a GLP-1 molecule of the present invention. Preferably, a divalent metal cationic salt such as zinc chloride is provided in excess to provide a molar ratio of up to about 50 molecules of a divalent metal cation for each molecule of GLP-1 substrate.

The temperature employed in this step is that which is sufficient to effect completion of the reaction. Typically, the reaction is run at ambient temperature.

The product of the present reaction, a crystalline or amorphous suspension, is isolated and purified using standard techniques.

The present invention also provides pharmaceutical compositions comprising a compound of the present invention in combination with a pharmaceutically acceptable carrier, diluent, or excipient. Such pharmaceutical compositions are prepared in a manner well known in the pharmaceutical art, and are administered individually or in combination with other therapeutic agents, preferably via parenteral routes. Especially preferred routes include intramuscular and subcutaneous administration.

Parenteral daily dosages, preferably a single, daily dose, are in the range from about 1 pg/kg to about 1,000 µg/kg of bodyweight, although lower or higher dosages may be administered. The required dosage will depend upon the severity of the condition of the patient and upon such criteria as the patient's height, weight, sex, age, and medical history.

In making the compositions of the present invention, the active ingredient, which comprises at least one compound of the present invention, is usually mixed with an excipient or diluted by an excipient. When an excipient is used as a diluent, it may be a solid, semi-solid, or liquid material which acts as a vehicle, carrier, or medium for the active ingredient.

In preparing a formulation, it may be necessary to mill the active compound to provide the appropriate particle size prior to combining with the other ingredients. If the active compound is substantially insoluble, it ordinarily is milled to particle size of less than about 200 mesh. If the active compound is substantially water soluble, the particle size is normally adjusted by milling to provide a substantially uniform distribution in the formulation, e.g., about 40 mesh.

Some examples of suitable excipients include lactose, dextrose, sucrose, trehalose, sorbitol, and mannitol. The compositions of the invention can be formulated so as to provide quick, sustained or delayed release of the active ingredient after administration to the patient by employing procedures well known in the art.

The compositions are preferably formulated in a unit dosage form with each dosage normally containing from about 50 µg to about 100 mg, more usually from about 1 mg to about 10 mg of the active ingredient. The term "unit dosage form" refers to physically discrete units suitable as unitary dosages for human subjects and other mammals, each unit containing a predetermined quantity of active material calculated to produce the desired therapeutic effect in association with a suitable pharmaceutical excipient.

For the purpose of parenteral administration, compositions containing a compound of the present invention preferably are combined with distilled water and the pH is adjusted to about 6.0 to about 9.0.

Additional pharmaceutical methods may be employed to control the duration of action. Controlled release preparations may be achieved by the use of polymers to complex or absorb a compound of the present invention. The controlled delivery may be exercised by selecting appropriate macromolecules (for example, polyesters, polyamino acids, polyvinylpyrrolidone, ethylenevinyl acetate, methylcellulose, carboxymethylcellulose, and protamine sulfate) and the concentration of macromolecules as well as the methods of incorporation in order to control release.

Another possible method to control the duration of action by controlled release preparations is to incorporate a compound of the present invention into particles of a polymeric material such as polyesters, polyamino acids, hydrogels, poly (lactic acid) or ethylene vinylacetate copolymers.

Alternatively, instead of incorporating a compound into these polymeric particles, it is possible to entrap a compound of the present invention in microcapsules prepared, for example, by coacervation techniques or by interfacial polymerization, for example, hydroxymethylcellulose or gelatin-microcapsules, respectively, or in colloidal drug delivery systems, for example, liposomes, albumin microspheres, microemulsions, nanoparticles, and nanocapsules, or in macroemulsions. Such teachings are disclosed in *Remington's Pharmaceutical Sciences* (1980).

The compounds of the present invention have insulinotropic activity. Thus, another aspect of the present invention provides a method for enhancing the expression of insulin comprising providing to a mammalian pancreatic B-type islet cell an effective amount of a compound of the present invention.

Similarly, the present invention provides a method for treating maturity onset diabetes mellitus in a meal, preferably a human, in need of such treatment comprising administering an effective amount of a compound or composition of the present invention, to such a meal.

The following examples are provided to further illustrate the present invention. It is not intended that the invention be limited in scope by reason of any of the following examples.

EXAMPLE 1

Individual aliquots of 5 different GLP-1 molecules were prepared by well-known, solid phase peptide synthesis and were lyophilized in small vials. Portions of 0.1M HEPES (N-[2-hydroxyethyl]piperazine-N'-[2-ethanesulfonic acid]) buffers at pH 7.4 containing various levels of zinc chloride were added to the aliquots to obtain a protein concentration of about 0.1 mg/mL. The samples were mixed and stored at ambient temperature (22° C.) for about 18 hours. The mixtures were then centrifuged (Fisher Model 235C microcentrifuge) for 5 minutes. The clear supernatants were pipetted from the tubes. The protein content of the supernatants was estimated by measuring their absorbance at 280 nm in a spectrophotometer (Gilford 260). The theoretical absorbance value for a 0.1.mg/mL solution of the GLP-1 molecules at this wavelength in the 1 cm cuvettes is 0.207. The results of this experiment are shown in Table 1.

TABLE 1

| Zn/GLP-1 Molecule Molar Ratio | 280 nm Absorbance | | | | |
|---|---|---|---|---|---|
| | GLP-1 (7-36)NH$_2$ | Gly$^8$—GLP-1 (7-36)NH$_2$ | Val$^8$—GLP-1 (7-37)OH | α-methyl-Ala$^8$—GLP-1 (7-36)NH$_2$ | Gly$^8$—Gln$^{21}$ GLP-1 (7-37)OH |
| 0 | 0.172 | 0.136 | 0.187 | 0.163 | 0.167 |
| 0.3 | 0.099 | 0.079 | 0.191 | 0.134 | 0.113 |
| 0.5 | 0.057 | .0.070 | 0.184 | 0.098 | 0.082 |
| 0.7 | 0.035 | 0.058 | 0.180 | 0.079 | 0.069 |
| 1.0 | 0.039 | 0.057 | 0.173 | 0.076 | 0.065 |
| 3.0 | 0.048 | 0.044 | 0.110 | 0.055 | 0.055 |

This example shows that only a small quantity of zinc is required to complex with and precipitate a significant portion of the GLP-1 molecules from these dilute solutions.

EXAMPLE 2

5 mg of GLP-1 (7-36)NH$_2$ was completely dissolved in 2.5 mL of pH 7.4, zinc-free 0.1M HEPES buffer. An additional 2.5 mL of pH 7.4, 0.1M HEPES buffer containing 0.6 mM zinc chloride was quickly added. The approximate molar ratio of zinc to GLP-1 (7-36)NH$_2$ in this sample is 1 to 1. The solution immediately became cloudy and precipitation soon formed. The mixture was stored at ambient temperature (22° C.) for 18 hours.

The precipitate became firmly attached to the bottom of the glass vial. The supernatant was completely decanted by pipette. The precipitate was then completely dissolved in 5.0 mL of 0.01N hydrochloric acid. The absorbance at 280 run was determined for both the supernatant and redissolved precipitate solutions. The zinc levels in these solutions were quantitated by atomic absorption spectrophotometry. The results of this experiment are shown in Table 2.

TABLE 2

| | 280 nm Absorbance | Zinc Concentration in Parts per Million |
|---|---|---|
| Supernatant (5 ml) | 0.118 | 9.02 |
| Redissolved Precipitate (5 ml) | 1.932 | 13.3 |

This example shows that most of the GLP-1 (7-36)NH$_2$ precipitated from the solution when the zinc-containing HEPES solution was added. The 280 nm absorbance value of 1.932 indicates the GLP-1 (7-36)NH$_2$ concentration of the redissolved precipitate is 0.933 mg/ml, or 283 μM. The zinc concentration of this same solution, 13.3 parts per million, is equivalent to a zinc concentration of 203 μM. Therefore, the molar ratio of zinc to GLP-1 (7-36)NH$_2$ in the precipitate was 0.717 to 1.

We claim:

1. A compound of the formula:

R$_1$-X-Glu-Gly-Thr-Phe-Thr-Ser-Asp-Val-Ser-Ser-Tyr-Leu-Y-Gly-Gln-Ala-Ala-Lys-Z-Phe-Ile-Ala-Trp-Leu-Val-Lys-Gly-Arg-R$_2$ (SEQ ID NO: 1)

wherein:

R$_1$ is L-histidine;
X is Val;
Y is Glu:
Z is Glu; and,
R$_2$ is Gly-OH.

2. A method of treating maturity onset diabetes mellitus which comprises administering to a mammal in need of such treatment an effective amount of a compound according to claim 1 to said mammal.

3. A pharmaceutical formulation which comprises the compound of claim 1 associated with one or more pharmaceutically acceptable carriers, diluents or excipients.

4. A method for enhancing the expression of insulin comprising providing to a mammalian pancreatic B-type islet cell an effective amount of the compound of claim 1.

* * * * *

UNITED STATES PATENT AND TRADEMARK OFFICE
CERTIFICATE OF CORRECTION

PATENT NO. : 5,705,483

DATED : January 6, 1998

INVENTOR(S) : John A. Galloway and James A. Hoffmann

It is certified that error appears in the above-indentified patent and that said Letters Patent is hereby corrected as shown below:

Column 1, line 14, reads ..."diabetes mellitus in a meal"... should read -diabetes mellitus in a mammal- Column 3, line 8, reads ..."*Clin. Therap.*, 12:460="... should read - *Clin. Therap.*, 12:460- -.

Column 5, line 22, reads ..."α-methly-Ala$^8$-GLP-1(7-36)NH$_2$"... should read - α-methly-Ala$^8$-GLP-1(7-36)NH$_2$ --

Column 7, line 36, reads ..."Owa, T., et aI."... should read - --Owa, T, et al.,--

Column 7, line 57, reads ..."Ser$^{22}$-Art$^{23}$-Arg24-Gln$^{26}$-GLP-1(7-37)"... should read, - Ser$^{22}$-Arg$^{23}$-Arg$^{24}$-Gln$^{26}$-GLP-1(7-37)-.

Column 12, lines 2-3, read ..."absorbance at 280 run in a"... should read, =absorbance at 280 nm in a-.

Column 12, line 42, reads ..."absorbance at 280 run"... should read, -absorbance at 280 mn-.

Signed and Sealed this

Thirteenth Day of March, 2001

NICHOLAS P. GODICI

*Attest:*

*Attesting Officer*        *Acting Director of the United States Patent and Trademark Office*